(12) United States Patent
Seeboth et al.

(10) Patent No.: US 8,957,155 B2
(45) Date of Patent: Feb. 17, 2015

(54) BLOCKED MERCAPTOSILANE COUPLING AGENT

(75) Inventors: Nicolas Seeboth, Clermont-Ferrand (FR); Karine Longchambon, Beaumont (FR); Laure Belin, Riom (FR); José Carlos Araujo Da Silva, Pont du Chateau (FR)

(73) Assignees: Compagnie Generale des Etablissements, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 792 days.

(21) Appl. No.: 13/141,511

(22) PCT Filed: Dec. 18, 2009

(86) PCT No.: PCT/EP2009/067554
§ 371 (c)(1),
(2), (4) Date: Aug. 19, 2011

(87) PCT Pub. No.: WO2010/072685
PCT Pub. Date: Jul. 1, 2010

(65) Prior Publication Data
US 2011/0294953 A1    Dec. 1, 2011

(30) Foreign Application Priority Data

Dec. 22, 2008   (FR) ..................................... 08 58931

(51) Int. Cl.
*C08F 8/42*       (2006.01)
*C07F 7/18*       (2006.01)

(52) U.S. Cl.
CPC ..................................... *C07F 7/184* (2013.01)
USPC .......................................... 525/102; 556/429

(58) Field of Classification Search
USPC .......................................... 525/102; 556/429
See application file for complete search history.

(56) References Cited

U.S. PATENT DOCUMENTS

| | | | |
|---|---|---|---|
| 3,842,111 A | 10/1974 | Meyer-Simon | |
| 3,873,489 A | 3/1975 | Thurn et al. | |
| 3,997,581 A | 12/1976 | Pletka et al. | |
| 4,002,594 A | 1/1977 | Fetterman | |
| 5,227,425 A | 7/1993 | Rauline | |
| 5,650,457 A | 7/1997 | Scholl et al. | |
| 5,733,963 A | 3/1998 | Sandstrom et al. | |
| 5,852,099 A | 12/1998 | Vanel | |
| 5,900,449 A | 5/1999 | Custodero et al. | |
| 6,191,205 B1 | 2/2001 | Micouin et al. | |
| 6,313,205 B1 | 11/2001 | Chiron et al. | |
| 6,420,488 B1 | 7/2002 | Penot | |
| 6,610,261 B1 | 8/2003 | Custodero et al. | |
| 6,765,045 B1 | 7/2004 | Daniel et al. | |
| 2001/0034389 A1 | 10/2001 | Vasseur | |
| 2001/0039308 A1 | 11/2001 | Custodero et al. | |
| 2001/0056138 A1 | 12/2001 | Vasseur | |
| 2002/0004549 A1 | 1/2002 | Custodero et al. | |
| 2002/0115767 A1 | 8/2002 | Cruse et al. | |
| 2005/0245754 A1 * | 11/2005 | Glatzer et al. | ............... 556/426 |

FOREIGN PATENT DOCUMENTS

| | | | |
|---|---|---|---|
| DE | 199 51 281 A1 | 4/2001 | |
| EP | 0 501 227 A1 | 9/1992 | |
| EP | 0 680 997 A1 | 11/1995 | |
| EP | 0 735 088 A1 | 10/1996 | |
| EP | 0 791 622 A1 | 8/1997 | |
| EP | 0 810 258 A1 | 12/1997 | |
| EP | 0 881 252 A1 | 12/1998 | |
| EP | 1 043 357 A1 | 10/2000 | |
| FR | 2 094 859 A | 2/1972 | |
| FR | 2 149 339 A | 3/1973 | |
| FR | 2 206 330 A | 6/1974 | |
| GB | 1 310 379 | 3/1973 | |
| WO | WO 99/02590 | 1/1999 | |
| WO | WO 99/02601 | 1/1999 | |
| WO | WO 99/02602 | 1/1999 | |
| WO | WO 99/28376 | 6/1999 | |
| WO | WO 00/05300 | 2/2000 | |
| WO | WO 00/05301 | 2/2000 | |
| WO | WO 00/53671 A1 | 9/2000 | |
| WO | WO 00/73372 A1 | 12/2000 | |
| WO | WO 00/73373 A1 | 12/2000 | |

(Continued)

OTHER PUBLICATIONS

International Search Report (PCT/ISA/210) issued on Feb. 22, 2010, by European Patent Office as the International Searching Authority for International Application No. PCT/EP2009/067554.

(Continued)

*Primary Examiner* — Ling Choi
*Assistant Examiner* — Chun-Cheng Wang
(74) *Attorney, Agent, or Firm* — Dickinson Wright PLLC

(57) ABSTRACT

The invention relates to a blocked mercaptosilane of general formula I below:

$$(HO)_2 R^1—Si—Z—S—C(=O)-A$$

in which:

$R^1$ represents a monovalent hydrocarbon-based group chosen from alkyls, which are linear or branched, cycloalkyls or aryls, having from 1 to 18 carbon atoms;

A represents hydrogen or a monovalent hydrocarbon-based group chosen from alkyls, which are linear or branched, cycloalkyls or aryls, having from 1 to 18 carbon atoms;

Z represents a divalent bonding group comprising from 1 to 18 carbon atoms.

13 Claims, No Drawings

(56) References Cited

FOREIGN PATENT DOCUMENTS

| | | |
|---|---|---|
| WO | WO 02/48256 | 6/2002 |
| WO | WO 2005/007660 A | 1/2005 |

OTHER PUBLICATIONS

Written Opinion (PCT/ISA/237) issued on Feb. 22, 2010, by European Patent Office as the International Searching Authority for International Application No. PCT/EP2009/067554.

* cited by examiner

BLOCKED MERCAPTOSILANE COUPLING AGENT

The present invention relates to mercaptosilane coupling agents, which can especially be used for coupling reinforcing inorganic fillers and diene elastomers in rubber compositions intended, for example, for the manufacture of tyres.

It is generally known that in order to obtain the optimum reinforcing properties imparted by a filler, this filler should be present in the elastomer matrix in a final form that is both as finely divided as possible and as uniformly distributed as possible. However, such conditions can be achieved only if the filler has a very good capacity, on the one hand, to be incorporated into the matrix during the mixing with the elastomer and to deagglomerate, and, on the other hand, to disperse uniformly in this matrix.

As is well known, carbon black exhibits such capacities, which is not generally the case for inorganic fillers. Indeed, for reasons of mutual affinities, the inorganic filler particles, have an annoying tendency to agglomerate together in the elastomer matrix. These interactions have the harmful consequence of limiting the dispersion of the filler and thus of limiting the reinforcing properties to a level that is substantially below that which it would theoretically be possible to achieve if all the bonds (inorganic filler/elastomer) capable of being created during the compounding operation were actually obtained. Moreover, these interactions tend to increase the consistency in the raw state of the elastomer compositions, and thus to render the processing ("processability") thereof more difficult than in the presence of carbon black.

Ever since savings in fuel and the need to protect the environment have become a priority, it has however proved necessary to produce tyres that have a reduced rolling resistance without having a disadvantageous effect on their wear resistance. This has been made possible in particular by virtue of the discovery of novel rubber compositions reinforced with inorganic fillers specifically described as reinforcing that are capable of competing, from a reinforcing viewpoint, with a conventional tyre-grade carbon black, while giving these compositions a lower hysteresis, synonymous with a lower rolling resistance for the tyres comprising them.

Such rubber compositions, comprising reinforcing inorganic fillers of the siliceous or aluminous type have, for example, been described in the patents or patent applications EP-A-0501227 (or U.S. Pat. No. 5,227,425), EP-A-0735088 (or U.S. Pat. No. 5,852,099), EP-A-0810258 (or U.S. Pat. No. 5,900,449), EP-A-0881252, WO99/02590, WO99/02601, WO99/02602, WO99/28376, WO00/05300 and WO00/05301.

Mention will be made in particular to documents EP-A-0501227, EP-A-0735088 or EP-A-0881252 which disclose diene rubber compositions reinforced with highly dispersible precipitated silicas, such compositions making it possible to manufacture treads having a substantially improved rolling resistance, without adversely affecting the other properties, in particular the grip, endurance and wear resistance properties. Such compositions exhibiting such a compromise of contradictory properties are also described in applications EP-A-0810258 and WO99/28376, with, as reinforcing inorganic fillers, specific, highly dispersible aluminous fillers (aluminas or aluminium (oxide)hydroxides), or else in applications WO00/73372 and WO00/73373, which described specific titanium oxides of reinforcing type.

The use of these specific, highly dispersible inorganic fillers, whether as the predominant reinforcing filler or not, has certainly reduced the difficulties in processing rubber compositions containing them, but this processing nevertheless remains more difficult than for rubber compositions conventionally filled with carbon black.

In particular, it is necessary to use a coupling agent, also referred to as a bonding agent, the role of which is to provide the bonding between the surface of the inorganic filler particles and the elastomer, while facilitating the dispersion of this inorganic filler within the elastomer matrix.

It is recalled here that the expression "coupling agent" (inorganic filler/elastomer coupling agent) is understood, in a known manner, to mean an agent capable of establishing a sufficient bond, of chemical and/or physical nature, between the inorganic filler and the diene elastomer; such a coupling agent, which is at least bifunctional, has, for example, a simplified general formula "Y—W—X", in which:
  Y represents a functional group ("Y" function) which is capable of bonding physically and/or chemically to the inorganic filler, such a bond possibly being established, for example, between a silicon atom of the coupling agent and the surface hydroxyl (OH) groups of the inorganic filler (for example, the surface silanols when it is silica);
  X represents a functional group ("X" function) capable of bonding physically and/or chemically to the diene elastomer, for example via a sulphur atom; and
  W represents a divalent group allowing Y to be linked to X.

The coupling agents in particular must not be confused with simple agents for covering the inorganic filler which, in a known manner, may comprise the Y function that is active with respect to the inorganic filler but are devoid of the X function that is active with respect to the diene elastomer.

Coupling agents, in particular silica/diene elastomer coupling agents, have been described in a large number of documents, the most well known being bifunctional organosilanes bearing at least one alkoxyl function as the Y function, and, as the X function, at least one function capable of reacting with the diene elastomer such as for example a sulphurated (i.e., sulphur-containing) function.

Thus, it has been proposed in patent applications FR-A-2094859 or GB-A-1310379 to use a mercaptoalkoxysilane coupling agent for manufacturing tyre treads. It was rapidly demonstrated and it is today well known that mercaptoalkoxysilanes are capable of providing excellent silica/elastomer coupling properties, but that the industrial use of these coupling agents is not possible due to the very high reactivity of sulphurated functions of thiol —SH type (X functions) that very rapidly results, during the preparation of rubber compositions in an internal mixer, in premature vulcanizations also referred to as "scorching", in very high viscosities in the raw state, and ultimately in rubber compositions that are almost impossible to work and to process industrially. To illustrate this problem, mention may be made, for example, to documents FR-A-2206330, U.S. Pat. No. 3,873,489 and U.S. Pat. No. 4,002,594.

To overcome this drawback, it has been proposed to replace these mercaptoalkoxysilanes with alkoxysilane polysulphides, especially bis(alkoxylsilylpropyl) polysulphides as described in very many documents (see, for example, FR-A-2149339, FR-A-2206330, U.S. Pat. No. 3,842,111, U.S. Pat. No. 3,873,489, U.S. Pat. No. 3,997,581, EP-A-680997 or U.S. Pat. No. 5,650,457, EP-A-791622 or U.S. Pat. No. 5,733,963, DE-A-19951281 or EP-A-1043357 and WO00/53671). Among these polysulphides, mention should especially be made of bis(3-triethoxysilylpropyl) tetrasulphide (abbreviated to TESPT) and bis(3-triethoxysilylpropyl) disulphide (abbreviated to TESPD).

These alkoxysilane polysulphides, in particular TESPT, are generally considered to be the products that provide, for vulcanizates comprising a reinforcing inorganic filler, in particular silica, the best compromise in terms of scorch safety, ease of processing and reinforcing power. They are, in this respect, the most widely used coupling agents today in rubber compositions for tyres, even though they are relatively expensive and, furthermore, usually have to be used in a relatively large amount.

The vulcanization of diene elastomers by sulphur is widely used in the rubber industry, in particular in the tyre industry. In order to vulcanize diene elastomers, a relatively complex vulcanization system is used that comprises, in addition to sulphur, various vulcanization accelerators and also one or more vulcanization activators, very particularly derivatives of zinc such as zinc oxide (ZnO) or zinc salts of fatty acids such as zinc stearate.

A medium-term objective of tyre manufacturers is to eliminate zinc or its derivatives from their rubber formulations, due to the known, relatively toxic nature of these compounds, especially with respect to water and aquatic organisms (classification R50 according to European Directive 67/548/EEC of 9 Dec. 1996).

It is found, however, that the elimination of zinc oxide, specifically in rubber compositions reinforced with an inorganic filler such as silica, very greatly degrades the processability characteristics of the rubber compositions in the raw state, with a reduction in the scorch time that is unacceptable from an industrial point of view. It is recalled that the "scorch" phenomenon rapidly results, during the preparation of rubber compositions in an internal mixer, in premature vulcanizations ("scorching"), in very high viscosities in the raw state, and ultimately in rubber compositions that are almost impossible to work and to process industrially.

Yet, the TESPT coupling agent is not suitable for compositions that are zinc-free or almost zinc-free.

However, the Applicants have discovered, during their research, novel and specific blocked mercaptosilanes that, unexpectedly, make it possible to overcome all of these drawbacks and therefore, in particular, enable them to be used as coupling agents for rubber compositions reinforced with an inorganic filler such as silica, in the absence or presence of a very small amount of zinc without the latter being replaced by another metal and while protecting the rubber compositions from the problem of premature scorching during the industrial processing thereof.

It is recalled here that blocked mercaptosilanes, as is well-known to a person skilled in the art, are silane precursors that are capable of forming mercaptosilanes during the preparation of rubber compositions (see, for example, US 2002/0115767 A1 or international Application WO 02/48256). The molecules of these silane precursors, referred to hereinbelow as blocked mercaptosilanes, have a blocking group in place of the hydrogen atom of the corresponding mercaptosilane. The blocked mercaptosilanes are capable of being unblocked by replacing the blocking group with a hydrogen atom, during compounding and curing, in order to result in the formation of a more reactive mercaptosilane, defined as a silane having the molecular structure that contains at least one thiol (—SH) (mercapto-) group bonded to a carbon atom and at least one silicon atom. These blocked mercaptosilane coupling agents may be used alone or in the presence of a blocked mercaptosilane activator, the role of which is to initiate, accelerate or boost the activity of the blocked mercaptosilane.

Consequently, a first subject of the invention relates to a blocked mercaptosilane of general formula (I) below:

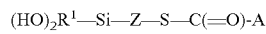

in which:
R$^1$, which are identical or different, each represent a monovalent hydrocarbon-based group chosen from alkyls, which are linear or branched, cycloalkyls or aryls, having from 1 to 18 carbon atoms;

A represents hydrogen or a monovalent hydrocarbon-based group chosen from alkyls, which are linear or branched, cycloalkyls or aryls, having from 1 to 18 carbon atoms;

Z represents a divalent bonding group comprising from 1 to 18 carbon atoms.

A further subject of the invention is a process for preparing a mercaptosilane of general formula (I) which comprises the following steps:
starting from a blocked mercaptosilane (hereinbelow product B) of formula (B):

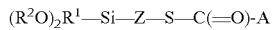

in which:
R$^1$, A and Z have the same meaning as in formula (I);
R$^2$, which are identical or different, represent a monovalent hydrocarbon-based group chosen from alkyls having from 1 to 6, preferably from 1 to 3;
a hydrolysis is carried out in an acid medium that makes it possible to result in the targeted blocked mercaptosilane of formula (I).

Another subject of the invention is the use, as coupling agent, of a blocked mercaptosilane in accordance with the invention, in particular as (inorganic filler/diene elastomer) coupling agent in a rubber composition.

I. MEASUREMENTS AND TESTS USED

The rubber compositions, in which the coupling agents are tested, are characterized, before and after curing, as indicated below.

I-1. Mooney Plasticity

Use is made of an oscillating consistometer as described in French Standard NF T 43-005 (1991). The Mooney plasticity measurement is carried out according to the following principle: the composition in the raw state (i.e., before curing) is moulded in a cylindrical chamber heated to 100° C. After preheating for one minute, the rotor rotates within the test specimen at 2 rpm and the working torque for maintaining this movement is measured after rotating for 4 minutes. The Mooney plasticity (ML 1+4) is expressed in "Mooney unit" (MU, with 1 MU=0.83 Newton.meter).

I-2. Scorch Time

The measurements are carried out at 130° C., in accordance with French Standard NF T 43-005. The change in the consistometric index as a function of time makes it possible to determine the scorch time of the rubber compositions, assessed in accordance with the abovementioned standard, by the parameter T5 (case of a large rotor), expressed in minutes, and defined as being the time necessary to obtain an increase in the consistometric index (expressed in MU) of 5 units above the minimum value measured for this index.

I-3. Dynamic Properties

The dynamic properties ΔG* and tan(δ)$_{max}$ are measured on a viscosity analyser (Metravib VA4000), in accordance with Standard ASTM D 5992-96. The response of a sample of vulcanized composition (cylindrical test specimen with a thickness of 4 mm and with a cross section of 400 mm$^2$), subjected to a sinusoidal stress in simple alternating shear, at a frequency of 10 Hz, at 23° C. or 40° C., is recorded. A scan with a strain amplitude ranging from 0.1 to 50% (forward cycle) then from 50% to 1% (return cycle) is carried out. The results made use of are the complex dynamic shear modulus (G*) and the loss factor (tan δ). For the return cycle, the maximum value of tan δ observed (tan(δ)$_{max}$), and also the difference in the complex modulus (ΔG*) between the values at 0.1% and 50% strain (the Payne effect) are indicated.

II. CONDITIONS FOR IMPLEMENTATION OF THE INVENTION

II-1. Blocked Mercaptosilane of the Invention

The first subject of the invention is a mercaptosilane of general formula (I):

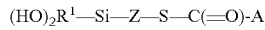

in which:
- $R^1$ represents a monovalent hydrocarbon-based group chosen from alkyls, which are linear or branched, cycloalkyls or aryls, having from 1 to 18 carbon atoms;
- A represents hydrogen or a monovalent hydrocarbon-based group chosen from alkyls, which are linear or branched, cycloalkyls or aryls, having from 1 to 18 carbon atoms;
- Z represents a divalent bonding group comprising from 1 to 18 carbon atoms.

Z may contain one or more heteroatoms chosen from O, S and N.

Advantageously:
- $R^1$ is chosen from methyl, ethyl, n-propyl and isopropyl, preferably from methyl and ethyl;
- A is chosen from alkyls having from 1 to 18 carbon atoms and the phenyl radical;
- Z is chosen from $C_1$-$C_{18}$ alkylenes and $C_6$-$C_{12}$ arylenes.

According to one embodiment, Z is chosen from $C_1$-$C_{10}$ alkylenes and more preferably Z is chosen from $C_1$-$C_4$ alkylenes.

According to another embodiment, $R^1$ is a methyl.

Preferably, A is chosen from alkyls having from 1 to 7 carbon atoms and the phenyl radical.

Mention will be made in particular of S-octanoylmercaptopropyldihydroxymethylsilane, the formula (I)° thereof is such that $R^1$ is a methyl, Z is a propylene and A is a heptyl.

II-2. Synthesis Process

The process in accordance with the invention for preparing a blocked mercaptosilane of formula (I) above comprises the following steps:

starting from a blocked mercaptosilane (hereinbelow product B) of formula (B):

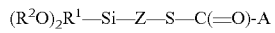

in which:
- $R^1$ represents a monovalent hydrocarbon-based group chosen from alkyls, which are linear or branched, cycloalkyls or aryls, having from 1 to 18 carbon atoms;
- $R^2$, which are identical or different, represent a monovalent hydrocarbon-based group chosen from alkyls having from 1 to 6, preferably from 1 to 3;
- A represents hydrogen or a monovalent hydrocarbon-based group chosen from alkyls, which are linear or branched, cycloalkyls or aryls, having from 1 to 18 carbon atoms;
- Z represents a divalent bonding group comprising from 1 to 18 carbon atoms.

It will be noted that the product B may especially be obtained from an "unblocked" mercaptosilane by making it undergo a thioesterification.

A hydrolysis is carried out in an acid medium that makes it possible to result in the targeted blocked mercaptosilane of formula (I).

II-3. Use as a Coupling Agent

As indicated above, the compound of the invention, by virtue of its dual functionality, finds an advantageous industrial application as a coupling agent, intended for example to provide the bonding or adhesion between a reactive polymer matrix (especially a rubber matrix) and any material with a hydroxylated surface, especially a mineral (for example, a glass fibre) or metallic (for example, a carbon steel or stainless steel wire) surface.

Without this being limiting, it may be used for coupling reinforcing inorganic or white fillers and diene elastomers, for example in rubber compositions intended for the manufacture of tyres. The expression "reinforcing inorganic filler" is understood, in a known manner, to mean an inorganic or mineral filler, whatever its colour and its origin (natural or synthetic), also known as "white filler" or sometimes "clear filler", in contrast to carbon black, this inorganic filler being capable of reinforcing by itself alone, without means other than an intermediate coupling agent, a rubber composition intended for the manufacture of tyres, in other words capable of replacing, in its reinforcing role, a conventional tyre-grade carbon black filler.

For such a use, the diene elastomer is then preferably chosen from the group of highly unsaturated diene elastomers consisting of polybutadienes (BRs), synthetic polyisoprenes (IRs), natural rubber (NR), butadiene-styrene copolymers (SBRs), butadiene-isoprene copolymers (BIRs), butadiene-acrylonitrile copolymers (NBRs), isoprene-styrene copolymers (SIRs), butadiene-styrene-isoprene copolymers (SBIRs) and blends of these elastomers.

When the monohydroxysilane of the invention is intended for (inorganic filler/diene elastomer) coupling in a rubber composition forming, for example, all or part of a passenger vehicle tyre tread, the diene elastomer is then preferably an SBR or a blend (mixture) of SBR and of another diene elastomer such as BR, NR or IR. In the case of an SBR elastomer, use is especially made of an SBR having a styrene content between 20% and 30% by weight, a content of vinyl bonds of the butadiene part of between 15% and 65%, a content of trans-1,4-bonds of between 15% and 75% and a glass transition temperature ($T_g$-measured according to the standard ASTM D3418-82) of between −20° C. and −55° C., this SBR copolymer, preferably prepared in solution (SSBR), optionally being used as a mixture with a polybutadiene (BR) preferably having more than 90% of cis-1,4-bonds.

When the tread is intended for a utility vehicle tyre, such as a heavy vehicle tyre, the diene elastomer is then preferably an isoprene elastomer, that is to say a diene elastomer chosen from the group consisting of natural rubber (NR), synthetic polyisoprenes (IRs), various isoprene copolymers and mixtures of these elastomers; it is then more preferably natural rubber or a synthetic polyisoprene of cis-1,4-type having a content (mol %) of cis-1,4-bonds of greater than 90%, more preferably still of greater than 98%.

The blocked mercaptosilanes of the invention have proved sufficiently effective by themselves for coupling a diene elastomer and a reinforcing inorganic filler such as silica, used at a preferred content of greater than 1 phr (parts by weight per hundred parts of elastomer), more preferably between 2 and 20 phr. They may advantageously constitute the sole coupling agent present in rubber compositions reinforced with inorganic filler and intended for the manufacture of tyres.

As reinforcing inorganic filler, mention will be made of mineral fillers of siliceous type, in particular silica ($SiO_2$), or of aluminous type, in particular alumina ($Al_2O_3$) or aluminium (oxide)hydroxides, or else reinforcing titanium oxides, as described in the aforementioned patents or patent applications.

III. EXEMPLARY EMBODIMENTS OF THE INVENTION

In the following tests, the invention is performed with a particular blocked mercaptosilane in accordance with the invention: S-octanoylmercaptopropyldihydroxymethylsilane.

III-1 Synthesis of S-Octanoylmercaptopropyldihydroxymethylsilane

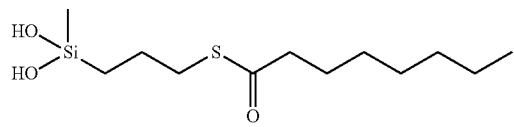 [SMILES: CCCCCCCC(=O)SCCC[Si](C)(O)O]

a) Preparation of S-octanoylmercaptopropyldimethoxymethylsilane with CAS number [828241-23-2]:

The intermediate product G may be prepared in a two-phase medium according to the procedure described in Application WO 2005/007660. Another possibility consists in preparing it according to the following procedure.

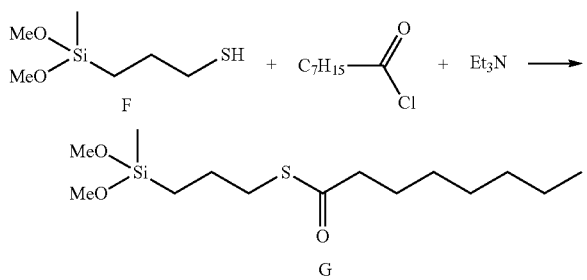

Octanoyl chloride (18.0 g, 0.111 mol) is added dropwise over 30 minutes to a solution of 3-mercaptopropyldimethoxymethylsilane F with CAS number [31001-77-1] (20.0 g, 0.111 mol) and triethylamine (11.2 g, 0.111 mol) in cyclohexane (200 mL) kept at 5° C. under an inert atmosphere. The temperature of the reaction medium remains between 5 and 8° C. The reaction medium is then stirred for 15 hours at room temperature. The precipitate of triethylamine hydrochloride $Et_3N.HCl$ is filtered over celite. After evaporating the solvents under reduced pressure at 25° C., S-octanoylmercaptopropyldimethoxymethylsilane G with CAS number [828241-23-2] (32.6 g, 0.106 mol) is obtained in the form of a colourless oil with a yield of 96%.

NMR analysis confirms the structure of the product obtained with a molar purity of 98%.

b) Preparation of S-octanoylmercaptopropyldihydroxymethylsilane:

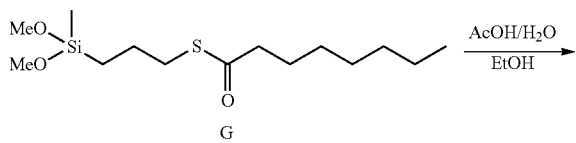

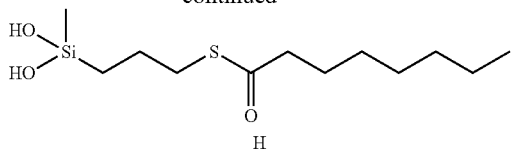

The S-octanoylmercaptopropyldimethoxymethylsilane G (42.0 g, 0.137 mol) is added to a mixture of 0.5% acetic acid, water (85 mL) and ethanol (250 mL). The solution is stirred for 4 hours at room temperature then the mixture is poured into a solution of sodium chloride (70 g) in water (1600 mL). The product is extracted with diethyl ether (2×250 mL). After evaporating the solvents under reduced pressure at 15° C., the solid obtained is recrystallized in pentane (400 mL) at −20° C. for 4 to 5 hours. The crystals are filtered and dried on the filter for 30 min, then 2-3 h under reduced pressure. The product obtained (24.9 g) has a melting point of 63° C. After evaporating the filtrate under reduced pressure at 15° C., the residue obtained is recrystallized a second time in pentane (80 mL) for 4-5 hours at −20° C. This second fraction (6.5 g) has a melting point of 63° C.

The two fractions are combined then recrystallized in a mixture of petroleum ether (600 mL) and ethanol (10 mL) for 12 hours. After filtering, then evaporating the residual solvents under reduced pressure for 2-3 hours, a white solid (25.8 g, 0.093 mol, 68% yield) having a melting point of 65° C. is obtained.

NMR analysis confirms the structure of the S-octanoylmercaptopropyldihydroxymethyl-silane H obtained with a molar purity of more than 93.5%.

If a higher purity is required, a final crystallization in a mixture of petroleum ether (500 mL) and ethanol (7 mL) for 15 hours makes it possible to obtain a solid (16.9 g, 44% yield) having a molar purity of more than 99% (melting point 66° C.).

III-2 Preparation of the Rubber Compositions

The tests which follow are carried out in the following way: the diene elastomer (SBR and BR blend), the silica, supplemented with a small amount of carbon black, the coupling agent and then, after kneading for one to two minutes, the various other ingredients, with the exception of the vulcanization system, are introduced into an internal mixer, 70% filled and having an initial vessel temperature of approximately 90° C. Thermomechanical working (non-productive phase) is then carried out in one stage (total duration of the kneading equal to approximately 5 min) until a maximum "dropping" temperature of approximately 165° C. is reached. The mixture thus obtained is recovered and cooled and then the covering agent (when the latter is present) and the vulcanization system (sulphur and sulphenamide accelerator) are added on an external mixer (homofinisher), at 70° C., the combined mixture being mixed (productive phase) for approximately 5 to 6 min.

The compositions thus obtained are subsequently calendered, either in the form of sheets (thickness of 2 to 3 mm) or of thin films of rubber, for the measurement of their physical or mechanical properties, or in the form of profiled elements which can be used directly, after cutting and/or assembling to the desired dimensions, for example as semi-finished products for tyres, in particular as tyre treads.

III-3 Characterization of the Rubber Compositions

The purpose of this test is to demonstrate the improved properties of rubber compositions which are free of zinc or that have zinc present, comprising a blocked mercaptosilane according to the invention, compared with a "conventional"

rubber composition comprising zinc and with rubber compositions that are free of zinc but that use coupling agents conventionally used in rubber compositions for tyre treads having silica as the reinforcing filler.

For this, 6 compositions based on a diene elastomer (SBR/BR blend), reinforced with a highly dispersible silica (HDS) are prepared, these compositions differing essentially in the following technical characteristics:

composition C1 is a "conventional" control composition containing zinc (1.5 phr of ZnO) and the compound TESPT (trade name: "Si69") as coupling agent;

composition C2 corresponds to composition C1 but is free of zinc;

composition C3 is free of zinc and comprises the compound MESPT (trade name: "RP74") frequently used in tyre treads, as coupling agent;

composition C4 is free of zinc and comprises a blocked mercaptosilane (trade name: "Silane NXT") different from the invention, as coupling agent;

composition C5 comprises, as coupling agent, a blocked mercaptosilane in accordance with the invention, S-octanoylmercaptopropyldihydroxymethylsilane, and is free of zinc;

composition C6 comprises, as coupling agent, a blocked mercaptosilane in accordance with the invention, S-octanoylmercaptopropyldihydroxymethylsilane, and also comprises zinc (1,5 phr of ZnO) in an identical manner to the conventional composition C1.

In order for the properties of compositions C1 to C6 to be comparable, the coupling agents of compositions C2 to C6 are used at a content that is isomolar in silicon compared to the control composition C1.

The conventional coupling agent used in the control composition C1 is TESPT. It is recalled that TESPT is bis(3-triethoxysilylpropyl) tetrasulphide having the structural formula (Et=ethyl):

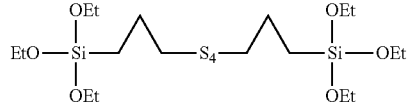

The coupling agent used in composition C3 is MESPT. It is recalled that MESPT is bis(3-dimethylethoxysilylpropyl) tetrasulphide having the structural formula (Et=ethyl):

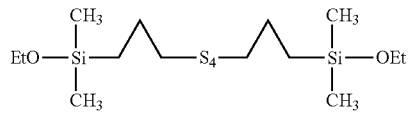

The coupling agent used in composition C4 is the silane NXT. It is recalled that NXT is S-octanoylmercaptopropyltriethoxysilane having the structural formula (Et=ethyl):

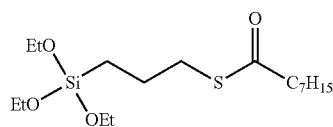

Tables 1 and 2 give the formulation of the various compositions (Table 1—content of the various products expressed in phr or parts by weight per hundred parts of elastomer) and also their properties before and after curing (around 40 min at 150° C.); the vulcanization system consists of sulphur and sulphenamide.

Examination of the results from Table 2 regarding the properties before curing firstly shows, compared to the control composition C-1 which contains the conventionally used content of zinc, that only the composition using the mercaptosilane in accordance with the invention, C5, makes it possible both to maintain an acceptable scorch time T5 (virtually identical to that of C1), while significantly improving the processability of the composition (much lower Mooney value than for composition C1).

The other compositions C2, C3 or C4 having properties that are unacceptable for the use thereof in tyres, due to a scorch time that is much too short and furthermore having, for compositions C2 and C3, a very high viscosity in the uncured state (very high Mooney value).

Furthermore, observation of the properties of these compositions after curing shows quite remarkably for composition C5 using the blocked mercaptosilane in accordance with the invention, compared to the control composition C1, a substantially reduced hysteresis, as attested to by values of $\tan(\delta)_{max}$ and $\Delta G^*$ which are substantially reduced. This is a recognized indicator of a reduction in the rolling resistance of the tyres, and consequently of a reduction in the energy consumption of motor vehicles fitted with such tyres.

It may be noted that composition C4, not in accordance with the invention, also has a reduced hysteresis relative to composition C1, however this property cannot be made use of in this case given the very short scorch time of composition C4 which renders it unusable in tyres.

Comparison of the conventional composition C1 and the composition in accordance with the invention C6 reveals the improvement in the processability properties (Mooney), in the scorch time (T5 greater than 30) and in the hysteresis (reduced values of $\tan(\delta)_{max}$ and $\Delta G^*$) for the composition in accordance with the invention C6.

It is therefore clear that even in a more conventional formulation, comprising zinc, the presence of a coupling agent in accordance with the invention allows a marked improvement in the properties that is indicative of the rubber composition comprising it.

It also clearly appears that a composition in accordance with the invention comprising, as coupling agent, a blocked mercaptosilane of formula (I) makes it possible to obtain properties that are equivalent, or even improved (processability, hysteresis) relative to the conventional control composition, without using zinc, unlike compositions comprising other coupling agents, including mercaptosilanes that are blocked but that have a different formula to that of the invention.

It may furthermore be noted that the use of a blocked mercaptosilane in accordance with the invention is particularly advantageous from the point of view of the environment. It makes it possible both to overcome the problems due to eliminating zinc and to solve the problem of releasing VOCs (volatile organic compounds). Indeed, the blocked mercaptosilane in accordance with the invention has no alkoxy groups (such as the ethoxy groups of TESPT) that are in fact the source of the release of alcohol (ethanol in the case of TESPT), both during the manufacture of the rubber compositions themselves and during the curing of the rubber articles incorporating these compositions.

TABLE 1

|  | Composition No. | | | | | |
| --- | --- | --- | --- | --- | --- | --- |
|  | C1 | C2 | C3 | C4 | C5 | C6 |
| SBR (1) | 70 | 70 | 70 | 70 | 70 | 70 |
| BR (2) | 30 | 30 | 30 | 30 | 30 | 30 |
| Silica (3) | 80 | 80 | 80 | 80 | 80 | 80 |
| coupling agent (4) | 6.4 | 6.4 | — | — | — | — |
| coupling agent (5) | — | — | 4.9 | — | — | — |
| coupling agent (6) | — | — | — | 8.9 | — | — |
| coupling agent (7) | — | — | — | — | 6.8 | 6.8 |
| carbon black (8) | 5 | 5 | 5 | 5 | 5 | 5 |
| MES oil (9) | 6 | 6 | 6 | 6 | 6 | 6 |
| plasticizing resin (10) | 20 | 20 | 20 | 20 | 20 | 20 |
| DPG (11) | 1.5 | 1.5 | 1.5 | 1.5 | 1.5 | 1.5 |
| anti-ozone wax (12) | 1.5 | 1.5 | 1.5 | 1.5 | 1.5 | 1.5 |
| ZnO (13) | 1.5 | — | — | — | — | 1.5 |
| antioxidant (14) | 2 | 2 | 2 | 2 | 2 | 2 |
| stearic acid (15) | 2 | 2 | 2 | 2 | 2 | 2 |
| sulphur | 1 | 1 | 1 | 1 | 1 | 1 |
| accelerator (16) | 2 | 2 | 2 | 2 | 2 | 2 |

(1) SSBR with 25% of styrene, 59% of 1,2-polybutadiene units and 20% of trans-1,4-polybutadiene units ($T_g = -24°$ C.); content expressed as dry SBR (SBR extended with 9% of MES oil, i.e. a total of SSBR + oil equal to 76 phr);
(2) BR (Nd) with 0.7% of 1,2-; 1.7% of trans-1,4-; 98% of cis-1,4-($T_g = -105°$ C.);
(3) "ZEOSIL 1165 MP" silica from Rhodia in the form of micropearls (BET and CTAB: around 150-160 m$^2$/g);
(4) TESPT ("SI69" from Degussa);
(5) MESPT ("RP74" from Rhodia);
(6) S-octanoylmercaptopropyltriethoxysilane ("Silane NXT ™" from GE Silicones);
(7) S-octanoylmercaptopropyldihydroxymethylsilane (synthesized product);
(8) N234 (Degussa);
(9) MES oil ("Catenex SNR" from Shell);
(10) polylimonene resin ("Dercolyte L120" from DRT);
(11) diphenylguanidine (Perkacit DPG from Flexsys);
(12) mixture of macrocrystalline and microcrystalline anti-ozone waxes;
(13) zinc oxide (industrial grade - Umicore);
(14) N-1,3-dimethylbutyl-N-phenyl-para-phenylenediamine ("Santoflex 6-PPD" from Flexsys);
(15) stearine ("Pristerene 4931" - Uniqema);
(16) N-cyclohexyl-2-benzothiazylsulphenamide ("Santocure CBS" from Flexsys).

TABLE 2

|  | Composition No. | | | | | |
| --- | --- | --- | --- | --- | --- | --- |
|  | C1 | C2 | C3 | C4 | C5 | C6 |
| Properties before curing | | | | | | |
| Mooney (MU) | 95 | 101 | 115 | 76 | 73 | 71 |
| T5 (min) | 18 | 11 | 14 | 12 | 16 | >30 |
| Properties after curing | | | | | | |
| ΔG* (MPa) | 5.81 | 5.27 | 4.39 | 3.59 | 4.61 | 4.42 |
| tan(δ)$_{max}$ | 0.354 | 0.362 | 0.346 | 0.331 | 0.351 | 0.326 |

The invention claimed is:

1. A blocked mercaptosilane of formula 1 below:

(HO)$_2$R$^1$—Si—Z—S—C(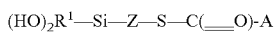O)-A wherein:
R$^1$ represents a monovalent hydrocarbon-based group selected from the group consisting of alkyls, which are linear or branched, having from 1 to 18 carbon atoms, and cycloalkyls and aryls having fewer than 18 carbon atoms;
A represents hydrogen or a monovalent hydrocarbon-based group selected from the group consisting of alkyls, which are linear or branched, having from 1 to 18 carbon atoms, and cycloalkyls and aryls having fewer than 18 carbon atoms;
Z represents a divalent bonding group comprising from 1 to 18 carbon atoms.

2. The blocked mercaptosilane according to claim 1, wherein Z contains one or more heteroatoms selected from the group consisting of O, S and N.

3. The blocked mercaptosilane according to claim 1, wherein:
R$^1$ is selected from the group consisting of methyl, ethyl, n-propyl and isopropyl;
A is selected from the group consisting of alkyls having from 1 to 18 carbon atoms and the phenyl radical;
Z is selected from the group consisting of C$_1$-C$_{18}$ alkylenes and C$_6$-C$_{12}$ arylenes.

4. The blocked mercaptosilane according to claim 3, wherein Z is selected from the group consisting of C$_1$-C$_{10}$ alkylenes.

5. The blocked mercaptosilane according to claim 4, wherein Z is selected from the group consisting of C$_1$-C$_4$ alkylenes.

6. The blocked mercaptosilane according to claim 3, wherein R$^1$ is methyl.

7. The blocked mercaptosilane according to claim 3, wherein A is selected from the group consisting of alkyls having from 1 to 7 carbon atoms and the phenyl radical.

8. The blocked mercaptosilane according to claim 3, wherein R$^1$ is methyl, Z is a propylene, and A is a heptyl.

9. A process for preparing a blocked mercaptosilane according to claim 1, comprising:
starting from a blocked mercaptosilane (hereinbelow product B) of formula (B):

(R$^2$O)$_2$R$^1$—Si—Z—S—C(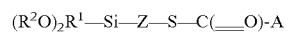O)-A wherein:
R$^1$, A and Z have the same meaning as in formula (I);
R$^2$, which are identical or different, represent a monovalent hydrocarbon-based group selected from the group consisting of alkyls having from 1 to 6 carbon atoms;
hydrolyzing product B in an acid medium to form the targeted blocked mercaptosilane of formula (I).

10. A method of coupling an inorganic filler with a diene elastomer comprising introducing a blocked mercaptosilane according to claim 1 into a mixture comprising inorganic filler and diene elastomer.

11. The method of coupling according to claim 10, wherein the mixture is in a rubber composition.

12. The process according to claim 9, wherein R$^2$ is selected from the group consisting of alkyls having from 1 to 3 carbon atoms.

13. The blocked mercaptosilane according to claim 3, wherein R$^1$ is selected from the group consisting of methyl and ethyl.

* * * * *